United States Patent [19]

Preece et al.

[11] Patent Number: 4,959,321

[45] Date of Patent: Sep. 25, 1990

[54] CELL FUSION APPARATUS

[76] Inventors: Alan W. Preece, Radiotherapy Centre, Horfield Road, Bristol, BS2 8ED, United Kingdom; Douglas H. Follett, Bristol General Hospital, Guinea Street, Bristol, BS1 6SP, United Kingdom

[21] Appl. No.: 322,349

[22] Filed: Mar. 13, 1989

[30] Foreign Application Priority Data

Mar. 26, 1988 [GB] United Kingdom ................. 8807271

[51] Int. Cl.⁵ .................. C12M 1/38; C12M 3/00; B01D 61/42
[52] U.S. Cl. ................... 435/284; 435/290; 935/93; 363/85; 204/180.1; 204/299 R
[58] Field of Search ............... 435/284, 287, 290, 316, 435/172.1, 172.2, 173; 935/89, 93; 204/180.1, 299 R, 242, 272; 363/85, 86

[56] References Cited

U.S. PATENT DOCUMENTS

| | | | |
|---|---|---|---|
| 4,476,004 | 10/1984 | Pohl | 204/299 R |
| 4,578,168 | 3/1986 | Hofmann | 204/272 X |
| 4,622,302 | 11/1986 | Sowers | 935/93 X |
| 4,695,547 | 9/1987 | Hilliard et al. | 204/242 X |
| 4,750,100 | 6/1988 | Ragsdale | 363/68 X |
| 4,764,473 | 8/1988 | Matschke | 204/272 X |
| 4,800,163 | 1/1989 | Hibi et al. | 204/299 R X |
| 4,804,450 | 2/1989 | Mochizuki et al. | 204/180.1 X |
| 4,832,814 | 5/1989 | Root | 204/180.1 X |

FOREIGN PATENT DOCUMENTS

| | | | |
|---|---|---|---|
| 0251877 | 12/1985 | Japan | 435/287 |
| 8706851 | 11/1987 | PCT Int'l Appl. | 204/180.1 |

OTHER PUBLICATIONS

U. Zimmermann et al., "Electric Field-Induced Cell-to-Cell Fusion", Journal of Membrane Biology, vol. 69, 1982, pp. 165-182.

*Primary Examiner*—Robert J. Warden
*Assistant Examiner*—Rebekah A. Griffith
*Attorney, Agent, or Firm*—Lee, Mann, Smith, McWilliams & Sweeney

[57] ABSTRACT

Cell electrofusion apparatus, for example for the production of hybridomas, comprises a flow-through capillary (14) surrounded by a water-cooled jacket (16) and through which a physiologically normal medium (such as a tissue culture fluid) containing cells is pulsed by a pump driven syringe (28), high voltage pulses being applied to electrodes (18) at opposite ends of the channel, which voltage pulses are of a magnitude and duration such that, taking into account the rate of fluid flow through the capillary and the extraction of heat by the cooling means, the temperature of the cell-containing medium is constrained to remain below the limit at which substantial cell damage occurs.

8 Claims, 2 Drawing Sheets

CELL FUSION APPARATUS

FIELD OF THE INVENTION

This invention relates generally to cell fusion apparatus and more particularly to apparatus for fusing cells by electrofusion, for example to produce hybridomas.

BACKGROUND OF THE INVENTION

Electrofusion is a known technique for causing cell hybridization by the application of a high voltage electric field to cells suspended in an electrically conducting medium. The cells may be brought into mutual contact, for example to group into long chains often known as pearl chain formations, by means such as the addition to the suspension of polyethylene glycol, or dielectrophoresis or charge modification procedures.

Field strengths required for electrofusion of cells are of the order of 300 to 400 kV/m. At such field strengths, a major relevant factor in the known process, carried out on a batch basis in a fusion chamber, is conductive heating, so that a low conductivity non-physiological supporting medium has necessarily had to be employed to avoid heat damage to the cells, together with non-ionic osmotic compensation, for example achieved by the use of mannitol or sucrose as the suspension medium, because osmotic stress also gives rise to low cell viability.

It is a primary object of this invention to provide improved apparatus for the electrofusion of cells, which apparatus permits a physiologically normal medium, i.e. a medium which is ionically and osmotically normal for cells, to be employed, with a consequent substantial increase in cell viability.

THE INVENTION

According to the invention, an apparatus for the electrofusion of cells comprises a flow channel of specific flow capacity for passage of cells suspended in a medium, cooling means surrounding the flow channel, electrodes at opposite ends of the flow channel, and a high voltage pulse generating circuit for applying DC voltage pulses to the electrodes while the medium is caused to flow slowly through the flow channel.

In use, the voltage pulses are applied at such a magnitude and at such a repetition rate, in relation to the flow capacity of the flow channel, rate of flow of the medium, and the rate of heat extraction by the cooling means, that the temperature rise of the cell containing medium is so limited that heat damage to the cells in the medium is substantially avoided.

Thus, the invention resides in a flow-through system with cooling wherein electrofusion is effected with DC voltage pulses defined to bring out a pulsed temperature rise limited to a specific maximum value, preferably 37 degrees C, of the cell containing medium, which may thus be constituted by a physiologically normal medium such as a tissue-culture fluid, with a consequent large improvement in cell viability. The invention enables the application of field strengths of 3 to 4 kV/cm, to a fluid which is ionically and osmotically normal for cells, and the temperature of the medium is limited without flowing the material sufficiently fast to disrupt aggregates of cells by shear forces. In use of the apparatus, cells may be aggregated in small clusters by the addition to the medium of a substance such as an antibody material, lectins, a surface-acting substance such as poly-L-lysine or attachment factors. As the fluid flow through the flow channel is preferably a pulsed flow timed in relation to voltage pulses, aggregation in small clusters is advantageous as compared with grouping in relatively long chains.

The invention lends itself in particular to the production of hybrid cells from spleen cells and myeloma cells, for the purpose of producing monoclonal antibodies.

BRIEF DESCRIPTION OF THE DRAWINGS

The apparatus in accordance with the invention is exemplified in the accompanying drawings, in which.

DESCRIPTION OF THE PREFERRED EMBODIMENTS

Figure 1:
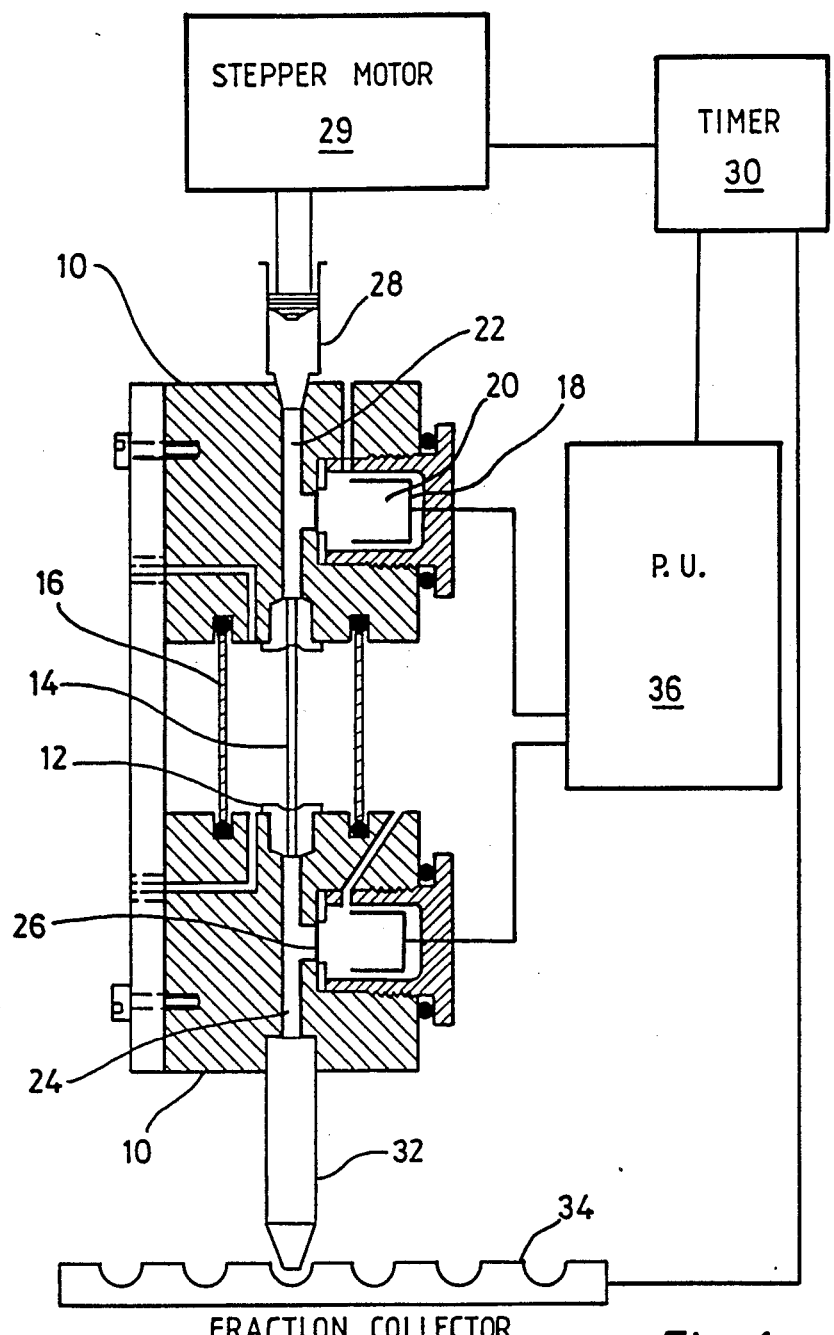
FIG. 1 is an elevational view of a practical embodiment.

FIG. 1 shows a flow-through cell consisting of upper and lower Teflon (Trade Mark) end blocks 10 which serve to locate, through silicone rubber seals carried by locating members 12, a flow channel 14 in the form of a glass capillary tube. The blocks 10 also serve to clamp in position a circulatory glass water jacket 16, surrounding the flow channel 14, the latter having a wall sufficiently thin to ensure efficient cooling of medium flowing through the channel by heat transfer to the circulating water in the surrounding jacket.

Electrodes 18 are disposed in an electrolyte 20 contained in chambers in the end blocks and separated from inlet/outlet passages 22, 24 in the end blocks 10 by semi-permeable membranes 26.

A 1 ml disposable syringe 28 connects with the inlet/outlet passsage 22 in the upper end block 10, and is adapted to be operated by a stepper motor 29 controlled from a timer 30 which in practice is constituted by a computerised control means. The inlet/outlet passage in the lower end block 10 connects with a disposable outlet tip 32, which can deliver samples to a fraction collector 34, for example comprising a 96 well micro-titre plate, advanced under supervision of the computerised control means 30.

A high voltage pulse generating circuit 36 applies DC voltage pulses, of a defined magnitude, duration and frequency, to the electrodes 18, again under supervision of the computerised control means 30.

In use, cooling water is circulated through the glass jacket 16, and cells suspended in tissue-culture fluid are passed through the capillary 14 from the disposable syringe 28 driven by the stepping motor 29. Each step triggers the pulse unit 36, which gives a high voltage (approx. 8Kv) pulse of defined length, applied to the electrodes 18 immersed in the electrolyte 20 contained in end block chambers.

After a group of pulses, the fraction collector 34 moves the microtitre plate to retrieve the pulsed sample. The rate of flow is defined by the removal of heat by the water in the water jacket, and the pulse size is defined by the temperature rise tolerated during the applied field. Both the sample syringe 28 and the outlet tip 32 are sterile disposable units.

In more detail, 1 ml is a suitable volume of cell containing medium (tissue-culture fluid). This is delivered by a syringe pump (stepper motor 29) driving a 1 ml disposable syringe (syringe 28) controlled by a microcomputer and interface (timer 30) to deliver 5 fluid pulses per microlitre. Software derived control pulse size are used to control the high voltage pulse generating unit 36 as well as the fraction collector 34.

The syringe 28 and the outlet tip 32 are coupled by the capillary 14, which is conveniently of 0.7 mm diameter with about 18 mm of its 22 mm length surrounded by the water jacket 16. The electrolyte side arms are separated from the medium at the 2 mm diameter end block passages 22, 24 by a cellulose membrane (semipermeable membrane 26) constituted by standard dialysis membrane "Viskin" tubing clamped by threaded hollow Teflon (Trade Mark) plugs screwing into the respective end blocks 10. The electrodes 18 are of platinum and are immersed in a 0.9% NaCl solution. Cooling water at 20 degrees C or less flows through the cooling jacket 16 at approximately 3 ml/minute. The tissue culture medium (approx. 0.9% NaCl) flowing through the capillary 14 has a resistivity of from 16 to 34 Kohms.

Referring to the mode of use in more detail, the instrument is filled manually with tissue culture fluid using a clean disposable syringe which is clipped into the syringe pump. The syringe is emptied under computer control and refilled with cell suspension (approx. $10^6$ cells) from a container placed under the disposable tip. The fluid (1 ml) is pulsed at 2 Hz and drawn in at 8 ul $sec^{-1}$ and redelivered to a microtitre plate at the same rate, re-pulsing the sample on the return path.

Limiting conditions generally applicable to the instrument are as follows:

Peak voltage=8 KV
Pulse length (75% points)=115 us
Fluid resistivity 0 16 K ohms at 20° C.
Peak current=0.5 amps
Power=4000 watts
Permitted temperature rise=17° C.
Tube volume=9 $\mu l$
At 1 pulse $sec^{-1}$
E=0.5 Joules=0.12 Cals
$\Delta T$ max=13° C. per pulse Heat transfer can be calculated, but it is assumed that the limiting conditions are the enclosed ends of the tube 14. At 9 ulsec$^{-1}$ flow this segment is flushed clear in approx. 0.2 second. Measurements with erythrocytes in saline show lysis occurring at 5–10Hz and the optimum rate was set at 2 Hz pulse rate and flow at 8 ul $sec^{-1}$. Moreover, in preliminary measurements carried out on Mouse myeloma cells X63 Ag8-653 and spleen cells, hybrids were obtained and viability at 5 Hz was 75–80%, and was unaffected by lower pulse rates.

Figure 2:
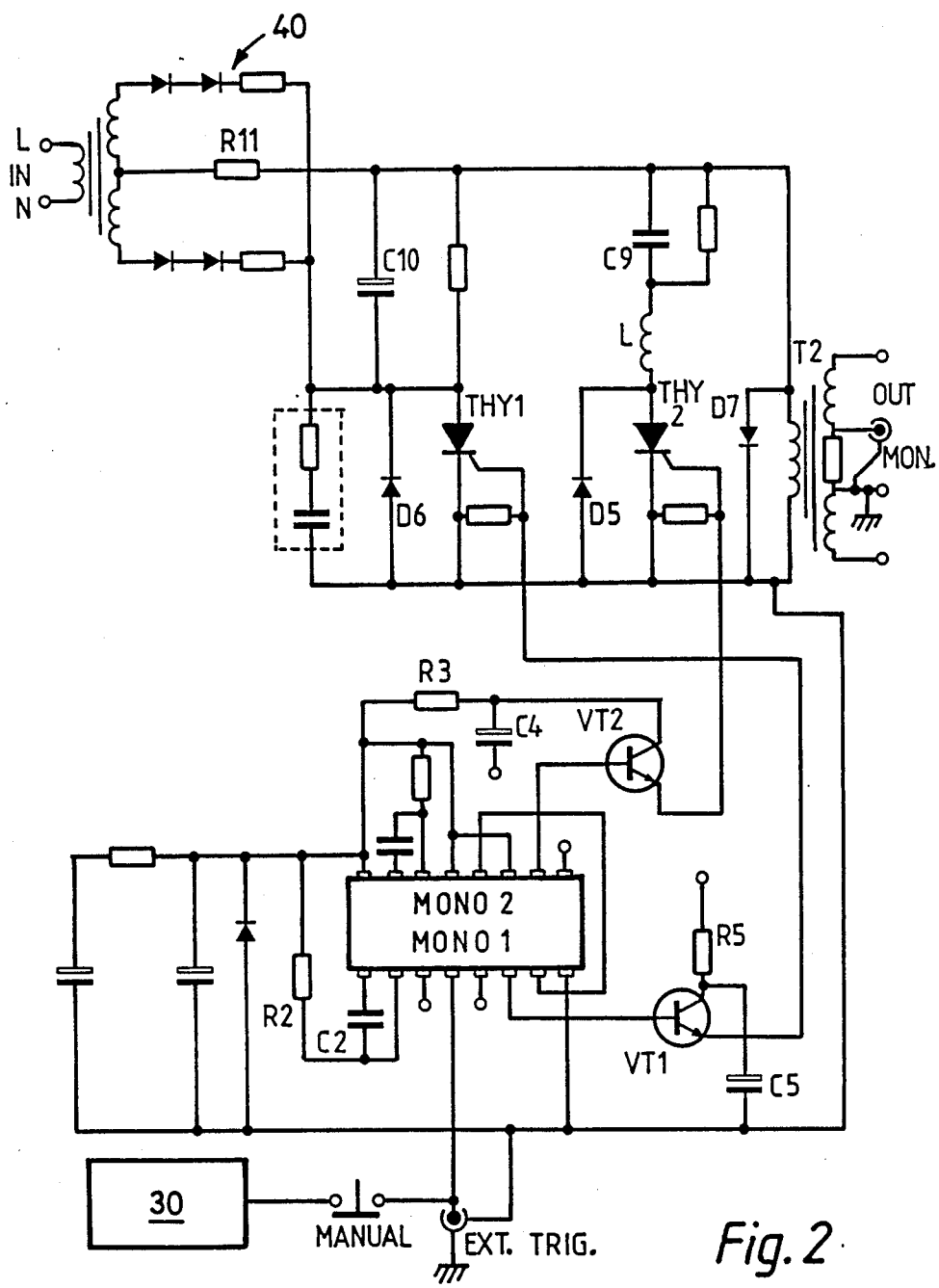
FIG. 2 is a simplified circuit diagram of a voltage pulse generating circuit.

A simplified circuit diagram of the high voltage generating circuit is given in FIG. 2. Briefly, a capacitor discharge thyristor chopper with transformer output is used to generate 8 KV, 100us pulses controlled by the microcomputer to give a fixed rate of pulsing for a given flow rate.

The main circuit is a two thyristor chopper with thyristor THY 1 discharging $C_{10}$ into the output transformer primary but being forcibly commutated off by THY 2. The circuit is arranged so that both thyristor cathodes are at zero volts and no gate trigger isolation is needed.

On applying mains voltage via rectifying circuit 40, $C_{10}$ is charged to 450V and 5V is provided for the logic circuits. THY 1 anode is then at +450V since $C_{10}$ negative is connected (for DC) to zero volts via T2 primary. When MONO 1 is triggered by the MANUAL button or an external trig pulse, a positive gate signal 75–100 us long (as determined by R2C2) is applied to THY 1 gate via VT 1.

THY 1 then conducts and a 450V negative step is applied to T2 primary. The same step appears on C9: D5 conducts and C9 with L rings for one half cycle leaving THY 2 anode about 200–300 V positive, with C9 charged to about 800 V.

At the end of the 75–100 us period, MONO 2 is triggered by MONO 1 Q output trailing edge and fires THY 2 via VT 2. The load current is diverted through THY 2 and C9 long enough to allow THY 1 to turn off. C9 then continues to discharge through THY 2 and T2 forming the trailing edge of the output pulse.

It is to be noted that rise and fall times at the output are limited at nominal max load of 0.5 A to about 30–40 us by leakage inductance of T2. However, this does result in a short-circuit on T2 secondary only giving peak primary currents about 80 amps, just within the thyristor ratings. R5-C5, R3-C4 isolate gate current from the +5 supply and also help to prevent any later mis-firings following the main pulse, whilst D6 protects THY 1 from reverse voltage and D7 clips overshoot on T2.

$R_{11}$ is selected to obtain +450V initially on $C_{10}$, whilst $R_2$ is selected for the required pulse length.

The complete unit includes a relay dump (not shown) and power supply generating circuits (also not shown).

In a practical embodiment, the instrument and controlling units will preferably be housed in an electrically interlocked cabinet, since it is well suited to fully automatic operation.

Various modifications of the above-described and illustrated embodiment are possible within the scope of the invention as defined by the appended claims.

We claim:

1. Apparatus for the electrofusion of cells comprising a flow channel of specific flow capacity for passage of cells suspended in a medium, the flow channel being mounted between end blocks containing inlet/outlet passages communicating with said flow channel, said inlet/outlet passages connecting at one end block with a syringe adapted to be driven by a stepper motor for producing a pulsed flow of the medium and at the other end with an outlet tip for feeding samples into a fraction collector, respectively, cooling means surrounding the flow channel, an electrode at each end of the flow channel, the electrodes being accommodated in electrolyte contained in electrolyte chambers formed in the respective end blocks, the electrolyte being separated from the inlet/outlet passages in the end blocks by semipermeable membranes, and a high voltage pulse generating circuit for applying DC voltage pulses to the electrodes while the medium is caused to flow slowly through the flow channel.

2. Apparatus according to claim 1, in which the applied voltage pulses are of such a magnitude and at such a repetition rate, in relation to the flow capacity of the flow channel, the rate of flow of the medium and the rate of heat extraction by the cooling means, that the temperature rise of the cell containing medium is so limited that heat damage to the cell containing medium is substantially avoided.

3. Apparatus according to claim 1, in which a controlling means for the apparatus limits the temperature of the cell containing medium to a maximum of 37 degrees C.

4. Apparatus according to claim 1, in which the peak magnitude of the applied voltage pulses is approximately 8 kV, providing a voltage gradient of about 4 kV/cm, and said applied voltage pulses have a duration of approximately 100 μs at a frequency not exceeding 10 Hz for a flow rate of the cell-containing medium of approximately 10 μl/sec.

5. Apparatus according to claim 1, in which the flow channel is of less than 1 mm diameter with a length of about 20 mm surrounded by the cooling means.

6. Apparatus according to claim 1, in which the cooling means is a circulatory water jacket.

7. Apparatus according to claim 1, in which the high voltage pulse generating circuit comprises a thyristor chopper having thyristors for controlling a capacitor discharging into the primary winding of an output transformer, and a triggerable control circuit for the thyristors.

8. Apparatus according to claim 7 including a computer for supplying first controlling pulses for triggering the control circuit high voltage pulse generator circuit and second controlling pulses, in timed relationship to the first controlling pulses, for triggering a control circuit for the stepper motor.

* * * * *